(12) United States Patent
Morrone et al.

(10) Patent No.: US 6,953,678 B1
(45) Date of Patent: Oct. 11, 2005

(54) USE OF ORTHOESTERS FOR THE SYNTHESIS OF CHIRAL ACIDS IN BIOCATALYZED IRREVERSIBLE ESTERIFICATION PROCESSES

(75) Inventors: Raffaele Morrone, Valverde (IT); Giovanni Nicolosi, Valverde (IT); Mario Piattelli, Valverde (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 326 days.

(21) Appl. No.: 10/048,120

(22) PCT Filed: Jul. 25, 2000

(86) PCT No.: PCT/EP00/07102

§ 371 (c)(1),
(2), (4) Date: Jun. 5, 2002

(87) PCT Pub. No.: WO01/07564

PCT Pub. Date: Feb. 1, 2001

(30) Foreign Application Priority Data

Jul. 26, 1999 (IT) .............................. ME99A0005

(51) Int. Cl.$^7$ .......................... C12P 17/00; C12P 17/10; C12P 7/62; C12N 1/14
(52) U.S. Cl. ...................... 435/117; 435/121; 435/134; 435/135; 435/146; 435/195; 435/196; 435/197; 435/280

(58) Field of Search .................. 435/117, 121, 134, 435/135, 136, 250, 195, 196, 197, 280

(56) References Cited

U.S. PATENT DOCUMENTS

| 4,107,439 | A | | 8/1978 | Walker et al. | |
|---|---|---|---|---|---|
| 4,888,433 | A | * | 12/1989 | Giordano et al. | 549/450 |
| 5,108,916 | A | * | 4/1992 | Cobbs et al. | 435/135 |
| 5,302,528 | A | * | 4/1994 | Battistel et al. | 435/280 |
| 5,580,783 | A | * | 12/1996 | Sariaslani et al. | 435/280 |
| 6,166,170 | A | * | 12/2000 | Putzig | 528/279 |
| 6,262,288 | B1 | * | 7/2001 | Fehr et al. | 556/440 |
| 6,372,929 | B1 | * | 4/2002 | Ridland et al. | 556/24 |

FOREIGN PATENT DOCUMENTS

| EP | 0 407 033 | 1/1991 |
|---|---|---|
| EP | 0 510 712 | 10/1992 |

* cited by examiner

Primary Examiner—Herbert J. Lilling
(74) Attorney, Agent, or Firm—Young & Thompson

(57) ABSTRACT

A process for the resolution of enantiomeric mixtures of a chiral carboxylic acid, including an esterification reaction of the carboxylic acid in an organic solvent, in the presence of a stereoselective hydrolase, characterized in that an orthoester of the formula $R^1$—$C(OR^2)_3$, in which $R^1$ is selected from H and $C_1$–$C_4$alkyl and $R^2$ is $C_1$–$C_8$alkyl or —$CH_2$—$C_{6-10}$aryl, is used as the esterification reactive.

8 Claims, 2 Drawing Sheets

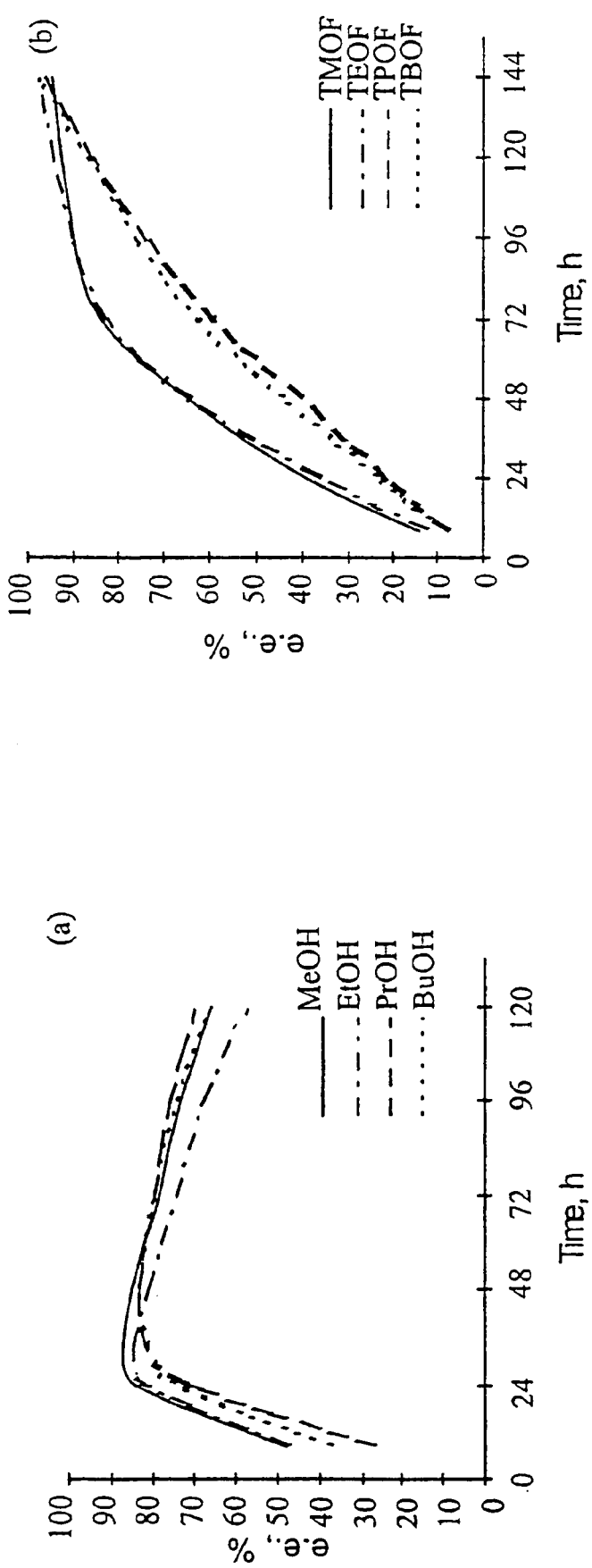
Fig. 1. Enantiomeric excess (ee) value of unreacted Flurbiprofen versus reaction time with different alcohols (a) and orthoformates (b)

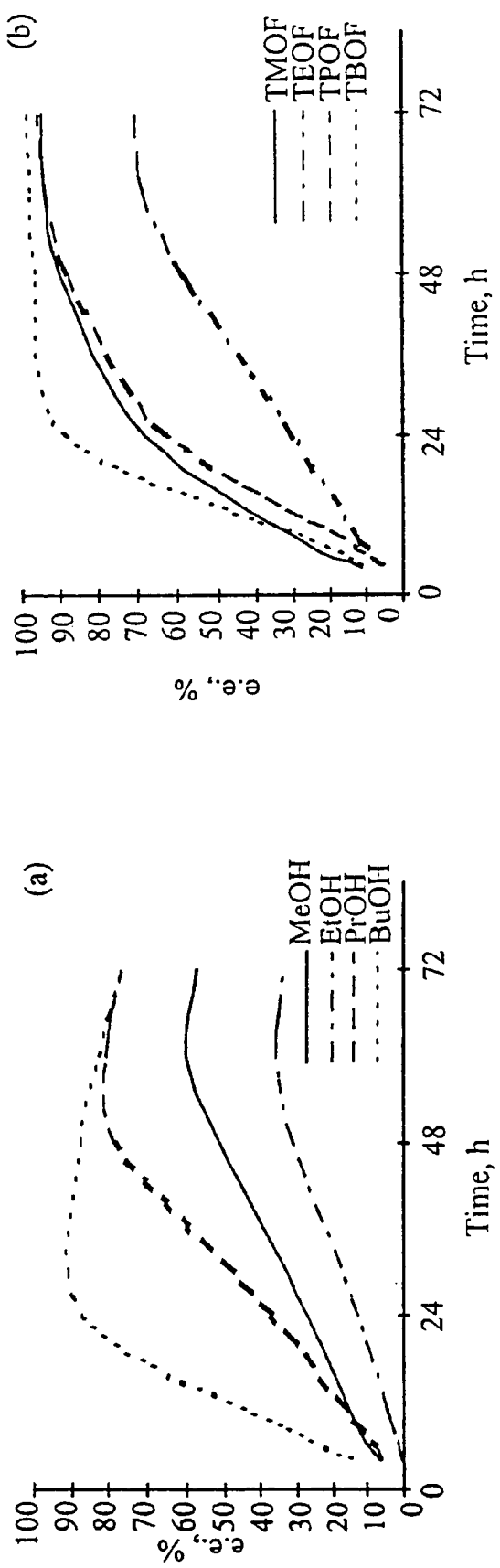
Fig. 2. Enantiomeric excess (ee) value of unreacted 2-Methylvaleric acid versus reaction time with different alcohols (a) and orthoformates (b)

USE OF ORTHOESTERS FOR THE SYNTHESIS OF CHIRAL ACIDS IN BIOCATALYZED IRREVERSIBLE ESTERIFICATION PROCESSES

Enantiomerically pure chiral compounds are increasingly required in recent times, as these compounds may be used in a number of different fields (biomedical, agroalimentary, special materials and the like). Racemic chiral acids may be resolved by means of esterification in organic solvent, catalyzed by a hydrolase (lipase, esterase, protease), as illustrated for example in IT 1 274 482 and IT 1 275458.

When a racemic acid RCOOH is reacted with an alcohol R'OH in the presence of a hydrolase with R-stereopreference, this enantiomer will be the fast reacting one, undergoing more rapidly the esterification, so that the unreacted acid will enrich in the S enantiomer, according to the following scheme:

Apparently, it seems possible to obtain the optically pure S isomer simply by extending the conversion to a sufficiently high value. However the reversibility of this reaction makes the situation complicated, as the R enantiomer, which is the faster formed one, is also the one more easily undergoing hydrolysis, to the detriment of the optical purities of both the R ester and the S acid residue (Chen, C. S.; Wu, S. H.; Girdaukas, G. and SiH, C. J. Am. Chem. Soc. 1987, 109, 2812–2817).

The above mentioned limits are also found in the desymmetrization of polycarboxylic acids meso-forms, when carrying out their enantiotoposelective esterification in the presence of hydrolase.

Many approaches have been proposed to overcome the problems connected with the reversibility of the esterification reaction:

a) Removing water from the reaction equilibrium by addition of dehydrating salts (Kvittingen, L.; Sjursnes, B. and Anthonsen, T. *Tetrahedron* 1992, 48, 2793–2802). The drawback of the process is that the collisions between the salt particles and the enzyme ones damage the latter, thus reducing the life times and making their recovery difficult.

b) Removing water from the equilibrium by addition of molecular sieves (Fonteyn, F.; Blecker, C.; Lognay, G.; Marlier, M. and Severin, M. *Biotechnol. Lett.* 1994, 16, 693–696). In addition to the above drawbacks, the alcohol also can be removed, particularly in case of low molecular alcohols.

c) Removing water by distillation. This method can be used only when water is the lower boiling component of the mixture; therefore it cannot be used with low boiling alcohols or solvents.

d) Recycle of the reaction products to increase their optical purity (Morrone, R.; Nicolosi, G.; Patti, A. and Piattelli, M. *Tetrahedron: Asymmetry* 1995, 6, 1773–1778). This method clearly increases the work up costs.

It has now been found, and this is the object of the invention, that when the reaction is carried out in the presence of orthoesters, the latter react with water formed during the reaction, making therefore the process irreversible.

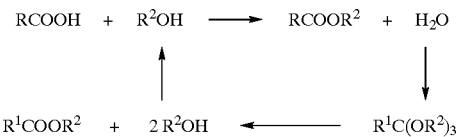

DISCLOSURE OF THE INVENTION

The present invention therefore provides a process for the resolution of enantiomeric mixtures of a chiral carboxylic acid of formula

R—COOH, wherein R is a hydrocarbon residue optionally containing one or more heteroatoms and optionally mono- or polysubstituted, comprising an esterification reaction of said carboxylic acid in an organic solvent, in the presence of a stereoselective hydrolase, characterized in that an orthoester of formula $R^1$—$C(OR^2)_3$, in which $R^1$ is selected from H and $C_1$–$C_4$alkyl and $R^2$ is $C_1$–$C_8$alkyl or —$CH_2$—$C_{6-10}$aryl, is used as the esterification reactive.

R is preferably the residue of an antiinflammatory arylpropionic acid such as (±)-(R,S)-2-(2-fluoro-4-biphenyl)-propionic, (±)-(R,S)-2-(3-benzoylphenyl)-propionic, (±)-(R,S)-2-(4-isobutylphenyl)-propionic, (±)-(R,S)-2-[4-(1-oxo-2-isoindolinyl)phenyl]propionic, (±)-(R,S)-2-[4-(2-thenoyl)phenyl]-propionic, (±)-(R,S)-2-(6-methoxy-2-naphthyl)-propionic acids.

$R^1$ is preferably selected from H, methyl, ethyl, n-propyl, n-butyl.

The stereoselective hydrolase is preferably a lipase from *Candida antarctica, Candida cylindracea, Pseudomonas cepacia, Mucor miehei, Mucor javanicus, Aspergillus niger*, swine pancreas, or a protease from *Aspergillus subtilis*.

The esterification reaction is generally carried out at a temperature of 0–50° C., preferably at 45° C. Similarly, a supercritical gas, such as $CO_2$, can be used as the reaction solvent.

Conveniently the process according to the invention comprises the step of adding to the reaction mixture, consisting of the carboxylic acid, the hydrolase and the organic solvent, an amount of water or of a alcohol with 1–8 carbon atoms equivalent to 1–5% mols compared with the mols of said chiral carboxylic acid. The reaction is thereby activated, which then proceeds thanks to the formation of the alcohol following reaction of the orthoester with the water formed during the esterification reaction.

The resulting suspension is kept under stirring at the optimal temperature for the enzyme used. The progress of the reaction can be monitored by the usual analytical methods known to those skilled in the art. When the desired conversion value, on which the desired enantiomeric excess of the products depends, has been reached, the reaction is stopped by filtering off the enzyme. The reaction products are then recovered by separation with procedures known to those skilled in the art.

Alternatively to the use of orthoesters, carbonates may also be used in the process of the invention.

The irreversibility of the esterification, carried out with the process of the invention, allows to prepare chiral acids in enantiopure form (in particular the enantiomer not preferred by the enzyme) by extending the reaction times up to conversion values higher than 50%.

FIG. 1a shows the change of the optical purity of the unreacted substrate in the esterification of rac-flurbiprofen, depending on the reaction time, when using methanol, ethanol, propanol and butanol as alcohol, acetonitrile as solvent and a lipase from Candida antarctica (with R stereopreference). In FIG. 1b it is reported the progress of the reaction, under the same operative conditions, using orthoformate (respectively methyl, ethyl, propyl, butyl) as alcohol source.

When comparing the progress of the reaction with alcohols (FIG. 1a) and that with orthoformates (FIG. 1b) it is easily evident that in normal esterification of flurbiprofen the ee of the unchanged substrate reaches a maximum value of 80–85 and then begins to drop.

In patent contrast, when orthoformates are used the ee value continues to increase by extending the incubation period and consequently the conversion value. With all the orthoformates tested, the ee value of the unreacted acid reaches 95–98%.

In FIG. 2 it is reported the trend for the esterification in hexane of 2-methylvaleric acid in the presence of Candida cylindracea lipase (Stereopreference S). The esterification with alcohol (FIG. 2a) shows the usual course of the reversible reactions and the ee of the residual acid decreased when conversion is extended much beyond 50%. The esterification with the use of orthoformates proceeded as an irreversible reaction (FIG. 2b) and with the best of the four tested, tributyl orthoformate, the ee values of the remaining substrate obtained is >98.

Obviously, the method proposed here can be used not only in the resolution of chiral acids, but also in the esterification of achiral acids, particularly when they are very expensive, to increase the yield by pushing the equilibrium toward completion.

The following examples disclose the invention in more detail.

EXAMPLE 1

Preparation of Enantiopure S-Flurbiprofen

Novozym 435[(R)] (lipase from Candida antartica) (100 g) was added to a solution of racemic flurbiprofen (41 mmol, 10 g) in $CH_3CN$ (1 1) containing tripropyl orthoformate (123 mmol, 26.5 ml) and 0.1 ml of n-propanol. The mixture was incubated at 45° C. under shaking (300 rpm) and conversion and ee of unreacted flurbiprofen were followed by hplc using a Chirex R-NGLY & DNB (250×4.0 mm) column. After 6 days conversion had reached 60% and the reaction was stopped filtering off the enzyme. Removal of the solvent in vacuo left a residue that was partitioned between hexane and aq. $NaHCO_3$ (3 g in 200 ml of water). The organic phase was washed with water, dried over $Na_2SO_4$ and the solvent removed to afford 6.8 g of (−)—R-flurbiprofen propyl ester (yield 58%, ee 64%). $^1$H NMR ($CDCl_3$): δ 0.89 (t, 3H, J=7 Hz) 1.54 (d, 3H, J=7 Hz), 1.65 (m,2H), 3.78 (q, 1H, J=7 Hz), 4.06 (t, 2H, J=6 Hz), 7.1–7.6 (m, 8H). Anal. Calcd for $C_{18}H_{19}FO_2$; C, 75.70; H, 6.69. Found: C. 75.62; H, 6.89.

Acidification of the aqueous phase with $H_2SO_4$ gave a precipitate of (±)—S-flurbiprofen (3.9 g, yield 39%, ee>98%). Anal. Calcd for $C_{15}H_{13}FO_2$; C, 73.76; H, 5.36. Found: C. 73.90; H, 5.52.

EXAMPLE 2

Preparation of Enantiopure (R)-2-Methylvaleric Acid

Candida cylindracea lipase (50 g) was added to a solution of racemic 2-methylvaleric acid (86.2 mmol, 10 g) in hexane (500 ml) containing tributyl orthoformate (86.2 mmol, 23 ml) and 0.1 ml of n-butanol. The mixture was incubated at 45° C. under shaking (300 rpm). Conversion and ee of the butyl ester were followed by GC using a β-cyclodextrin (dimethylpenthylbetacdx/OV1701 3:7) column. After 48 h conversion had reached 65% and reaction was stopped filtering off the enzyme. After partition with aq. $NaHCO_3$ (3 g in 200 ml of water) the hexane phase was dried over $Na_2SO_4$ and evaporated under vacuum to furnish 9.6 g of (S)-2-methylvaleric butyl ester (yield 65%, ee 53%). MS data agreed with those reported in the literature (Kim Ha, J.; Lindsay, R. C.; J. Food Compos. Anal. 1989, 2, 118–131). Anal. Calcd for $C_{10}H_{20}O_2$; C, 69.72; H, 11.70. Found: C. 69.98; H, 11.84.

The aqueous phase was acidified with $H_2SO_4$, extracted three times with hexane and the organic phase were pooled. Removing of hexane under vacuum gave 3.5 g of (R)-2-methylvaleric acid (yield 35%, ee>97%). $[a]_D^{20}$=18.2 (neat); (lit. $[a]_D^{20}$=18.4 (neat); Levene, P. A.; Marker, R. E. J. Biol. Chem. 1932, 98,1) Anal. Calcd for $C_6H_{12}O_2$; C, 62.04; H, 10.41. Found: C. 62.31; H, 10.52.

What is claimed is:

1. A process for the resolution of enantiomeric mixtures of a chiral carboxylic acid of formula R—COOH,
   wherein R is a hydrocarbon residue optionally containing one or more heteroatoms and optionally mono- or polysubstituted, comprising an esterification reaction of said carboxylic acid in an organic solvent, in the presence of a stereoselective hydrolase, and an orthoester of formula $R^1$—$C(OR^2)_3$,
   in which $R^1$ is selected from H and $C_1$–$C_4$alkyl and $R^2$ is $C_1$–$C_8$alkyl or —$CH_2$—$C_{6-10}$aryl, for the resolution of said enantiomeric mixture of said chiral carboxylic acid.

2. The process as claimed in claim 1, wherein $R^1$ is selected from H, methyl, ethyl, n-propyl, n-butyl.

3. The process as claimed in claim 2, wherein said stereoselective hydrolase is a lipase selected from Candida antarctica, Candida cylindracea, Pseudomonas cepacia, Mucor miehei, Mucor javanicus, Aspergillus niger, swine pancreas, or a protease from Aspergillus subtilis.

4. The process as claimed in claim 1, wherein said esterification reaction is carried out at a temperature of 0–50° C.

5. The process as claimed in claim 1, further comprising adding the reaction mixture with an amount of water or an alcohol with 1–8 carbon atoms equivalent to 1–5% mols compared with the mols of said chiral carboxylic acid.

6. The process as claimed in claim 1, wherein in said esterification reaction the meso form of a bicarboxylic acid acts as the substrate.

7. The process as claimed in claim 1, wherein said carboxylic acid is selected from (±)-(R,S)-2-(2-fluoro-4-biphenyl)-propionic, (±)-(R,S)-2-(3-benzoylphenyl)-propionic, (±)-(R,S)-2-(4-isobutylphenyl)-propionic, (±)-(R,S)-

2-[4-(1-oxo-2-isoindolinyl)phenyl] propionic, (±)-(R,S)-2-[4-(2-thenoyl)phenyl]-propionic, (±)-(R,S)-2-(6-methoxy-2-naphthyl)-propionic acids.

8. A process for the resolution of enantiomeric mixtures of a chiral carboxylic acid of formula R—COOH,
wherein R is a hydrocarbon residue optionally containing one or more heteroatoms and optionally mono- or polysubstituted,
comprising combining an amount of water or an alcohol having 1–8 carbon atoms equivalent to 1–5% mols of said chiral carboxylic mixture to said enantiomeric mixture, said enantiomeric mixture comprising said chiral carboxylic acid, an organic solvent, and a stereoselective hydrolase, in the presence of an orthoester of formula $R^1$—$C(OR^2)_3$, wherein $R^1$ is selected from H and $C_1$–$C_4$alkyl and $R^2$ is $C_1$–$C_8$alkyl or —$CH_2$—$C_{6-10}$aryl, for the resolution of said enantiomeric mixture of said chiral carboxylic acid.

* * * * *